United States Patent [19]

Stefano

[11] Patent Number: 5,556,751
[45] Date of Patent: Sep. 17, 1996

[54] SELECTIVE AMPLIFICATION SYSTEM USING Q-β REPLICASE

[75] Inventor: James E. Stefano, Hopkinton, Mass.

[73] Assignee: Amoco Corporation, Chicago, Ill.

[21] Appl. No.: 222,566

[22] Filed: Apr. 5, 1994

Related U.S. Application Data

[63] Continuation of Ser. No. 132,685, Oct. 6, 1993, abandoned, which is a continuation of Ser. No. 851,221, Mar. 10, 1992, abandoned, which is a continuation of Ser. No. 514,518, Apr. 25, 1991, abandoned.

[51] Int. Cl.⁶ .............................. C12P 19/34; C12Q 1/68
[52] U.S. Cl. ..................... 435/6; 435/91.1; 435/91.21; 435/91.3; 435/810; 536/25.3
[58] Field of Search ...................... 435/6, 91.1, 91.21, 435/91.3, 810; 436/501, 808; 536/25.3; 935/77, 78

[56] References Cited

U.S. PATENT DOCUMENTS

| | | | |
|---|---|---|---|
| 4,786,600 | 2/1988 | Kramer et al. | 435/320.1 |
| 4,868,105 | 5/1989 | Urdea et al. | 435/6 |
| 4,957,858 | 9/1990 | Chu et al. | 435/6 |
| 5,112,734 | 5/1992 | Kramer et al. | 435/6 |
| 5,356,774 | 10/1994 | Axelrod et al. | 435/6 |
| 5,364,760 | 11/1994 | Chu et al. | 435/6 |

FOREIGN PATENT DOCUMENTS

WO87/06270  3/1987  WIPO.

OTHER PUBLICATIONS

Bauer et al., *Proc. Natl. Acad. Sci. USA* 86: 7937 (1989).
Srinivasan, S. and Jaspars, E. M. J., *Biochim. et Biophys. Acta* 696: 260 (1982).
F. R. Kramer et al., *J. Mol. Biol.*, 89:719–736 (1974).
L. Eoyang and J. T. August, *Proc. Nucl. Acid. Res.*, 2:829–839 (1972).
H. Lomell et al., *Clin. Chem.*, 35(9):1826–1831 (1989).
M. Sumper and R. Luce, *Proc. Nat'l Acad. Sci U.S.A.*, 72(1):162–166 (1975).
D. R. Mills, *J. Mol. Biol.*, 206:489–500 (1988).
E. A. Miele et al., *J. Mol. Biol.*, 171:281–295 (1983).
B. C. F. Chu et al., *Nucl. Acids Res.*, 14(14):5591–5603 (1986).

*Primary Examiner*—Mary E. Mosher
*Assistant Examiner*—Laurie Scheiner
*Attorney, Agent, or Firm*—Norval B. Galloway

[57] ABSTRACT

Mutant forms of midivariant RNA are disclosed which are replicated efficiently by the enzyme Qβ replicase in the presence of an agent(s) which is useful for the real time, quantitative detection of the accumulating RNA products. This agent(s) also suppresses the replication of non-mutant wild type midivariant RNA. The mutant MDV RNAs, when modified by the addition of specific probe sequences, retain their replication properties in the presence of the detection agent. This method allows the replication to be monitored using a real time mode thereby providing a reliable method for monitoring the kinetics of the reaction, and determining the initial level of amplified RNA.

6 Claims, 13 Drawing Sheets

PIʳ MDV-1 Variant

Oligo #1

5' CCA-GAA-GCT-TGC-TAA-TAC-GAC-TCA-CTA-TAG-GGG-ACC-CCC-CCG-GAA-
         Hind III           T7 Promoter                              Sal I
GGG-GGG-GAC-GAG-GTG-CGG-GCA-CCT-CGT-ACG-GGA-GGT-CGA-CCG-TGA-
CTT-GTC-ACG-GGC-TAG-CGC-TTT-CGC-GCT-CTC-CCA-GGT-GAC-GCC-TCG-
                    Nhe I
TGA-AGA-G 3'

Oligo #2

Pst I      Sma I
5' GCA-GGT-ACC-TCG-AGG-ATC-CTG-CAG-AAT-TCC-CGG-GAA-CCC-CCC-TTC-
      Kpn I    Xho I   Bam HI            Eco RI
GGG-GGG-TCA-CCT-CGC-GCA-GCG-GGC-TGC-GCG-AAG-GGG-CCA-CGC-TGC-
GAA-GCA-GCG-TGG-CGG-TTC-TCG-TGC-GTT-ACC-GAA-ACG-CAC-GAA-GGT-
CAC-GCC-TCT-TCA-CGA-GG 3'

FIG. 6

MDV-SYN RNA 5,556,751

SELECTIVE AMPLIFICATION SYSTEM USING Q-β REPLICASE

This application is a continuation of application Ser. No. 08/132,685 filed Oct. 6, 1993, now abandoned, which is a continuation of application Ser. No. 07/851,221, filed Mar. 10, 1992, now abandoned, which is a File Wrapper Continuation of Ser. No. 07/514,518, filed Apr. 25, 1991, now abandoned.

BACKGROUND

Q Beta (Qβ) replicase is a template-specific RNA-directed RNA polymerase derived from the bacteriophage Qβ. In vivo, the normal function of Qβ replicase is to replicate the RNA genome of the Qβ bacteriophage to produce progeny phage genomes. Each infectious Qβ virion contains one molecule of single stranded RNA of molecular weight $1.5 \times 10^6$, which is termed the viral plus (+) strand. This is the strand utilized as mRNA to direct viral protein synthesis. Using the (+) strand as a template, Qβ replicase produces an RNA copy of the template which is complementary to the original template. These RNA molecules are termed minus (−) strands. Importantly, both the (+) and (−) strands are templates for the enzyme. Therefore, replication of the RNA template proceeds in a geometric fashion (i.e., 1, 2, 4, 8, 16, 32, etc.).

In vitro, the enzyme can utilize a limited number of other RNA molecules besides the Qβ genome as templates. One such RNA template which has been relatively well studied is termed midivariant (MDV). MDV is significantly smaller than the Qβ RNA genome and was discovered as a naturally occurring product in Qβ replicase reactions. Significant effort has been invested in designing variants of MDV RNA which can serve as amplifiable reporter probes in nucleic acid hybridization assays.

In general terms, a reporter probe will serve two functions. It will contain a nucleotide sequence which permits it to hybridize specifically with a predetermined target nucleic acid, and it will contain a ligand of some sort which permits its detection in an assay. Common detection ligands are radioactive P-32 or I-125, fluorescein, or biotin which can be coupled to probe sequences in a variety of ways.

In the case of MDV reporter probes, a probe sequence is built into the MDV molecule in such a way that it: 1) permits the MDV probe to specifically hybridize to its intended target nucleic acid, and 2) remains replicatable by Qβ replicase in spite of the additional probe sequence. Thus, the MDV serves as an amplifiable detection ligand. One billion or more progeny molecules can be produced from a single starting template MDV molecule in approximately 30 minutes. Thus, a very large number of detection ligands (MDV RNA molecules) can be produced from very few hybridized reporter probes. This permits the development of extremely sensitive nucleic acid hybridization assays; that is, assays which are capable of detecting the presence of very few target molecules (or organisms) in a test sample.

A variety of engineered MDV probe molecules are described in U.S. Pat. No. 4,786,600, and patent applications Ser. Nos. 252,243 and 370,218, the teachings of which are incorporated herein by reference.

Assay sensitivity is a function not only of the amount of signal that can be generated for a given amount of target nucleic acid, but also of the amount of "background" signal which is generated even in the absence of target nucleic acid. One significant source of background signal in nucleic acid probe systems using Qβ replicase is the presence in some Qβ replicase preparations of contaminating RNA termed "wild-type" or "endogenous" variant RNA. Qβ replicase prepared by the procedure of Eoyang and August typically contains between 100 and 10,000 molecules of wild type variant RNA per microgram of protein. Eoyang and August, *Prog. Nucl. Acids Res.*, 2:829–839 (1972). This wild type variant RNA replicates and generates a signal even when exogenous (i.e., probe) template RNA is omitted from the reaction. This wild type variant RNA competes with the probe RNA for Qβ replicase, severely limiting the enzyme's ability to replicate low numbers of probe RNAs to detectable levels. This, in turn, limits the achievable sensitivity of the assay to some value above the background level of wild type variant RNA.

One means of limiting this background signal would be to improve the purification of the Qβ replicase enzyme so that it contains less (or no) contaminating wild type variant RNA. DiFrancesco, in co-pending patent application U.S. Ser. No. 07/364,306, filed Jun. 9, 1989 which is incorporated herein by reference, discloses an improved Qβ replicase purification protocol which yields highly purified enzyme that appears to be free of wild type MDV RNA.

Another means of limiting assay background due to wild type MDV would be to devise recombinant MDV probe molecules and assay conditions that enhance the replication of probe molecules relative to that of wild type MDV molecules. Kramer et al., *J. Mol. Biol.* 89:719–736 (1974) describe a mutant MDV RNA whose replication is less sensitive than "wild type" (endogenous) MDV to the dye ethidium bromide. However, Kramer et al. do not discuss the use of such mutant MDV molecules as probes, A major consideration in the convenience and precision of assays employing Qβ replicase is detection of the amplified products. In vitro, Qβ replicase is capable of replicating one MDV molecule. However, it also is a property of Qβ replicase that the time course of the appearance of replication products reflects the amount of MDV template (or probe) present at the beginning of the reaction. That is, given a particular set of reaction conditions, a larger amount of input MDV will yield observable levels of product MDV sooner than lower input levels. In fact, there is a predictable, mathematical relationship between the input MDV and the time to observable product. Thus, there is significant value in monitoring the kinetics of the Qβ replicase reaction in that information about the level of target nucleic acid in the experimental sample can be inferred.

By careful selection of the inhibitory chemical agent, MDV probes can be designed which permit a convenient, quantitative, kinetic analysis of MDV production during the replication (amplification) reaction.

SUMMARY OF THE INVENTION

The invention relates to MDV probe constructs which replicate in the presence of particular inhibitory chemical agents, which agents inhibit replication of wild type MDV RNA, and to a method of selectively amplifying MDV RNA probe molecules in a Qβ replicase amplification system. The production and use of the novel MDV probe constructs is described. These probes simultaneously incorporate a number of advantages over any previously described probe molecules, including:

1) reduction of assay background signal which is due to replication of wild type MDV RNA molecules;

2) the ability to detect fewer molecules of probe in the presence of a chemical agent to which the probe is selectively resistant; and 3) the ability to perform convenient and quantitative real time measurements on Qβ replicase amplification assays.

The present probes are produced by linking mutant midivariant RNA (mutant MDV RNA), which is resistant to inhibition by agents which inhibit the replication of non-mutant wild type MDV RNA, to a nucleic acid probe sequence of choice to produce the recombinant MDV RNA probe. The recombinant MDV RNA probes then can be used in a Qβ replicase amplification system. In this method, the recombinant MDV RNA probe and an agent which inhibits the replication of wild type MDV RNA are included in the Qβ replicase amplification system, which is maintained under conditions appropriate for amplification of the recombinant MDV RNA probe. The replication of the wild type MDV RNA is suppressed by the inhibiting agent, while replication of the resistant recombinant MDV RNA probe proceeds. As a result, selective amplification of the recombinant MDV RNA probe and reduction of the replication of undesirable wild type midivariant occurs. Depending upon the position at which the probe sequence is inserted within the MDV (or mutant MDV), the probe sequence itself may or may not be amplified. If the probe sequence is inserted within the MDV sequence, then it is replicated (amplified), along with the MDV sequence. If the probe sequence is appended to either end of the MDV sequence, then it is not replicated along with the MDV sequence. In the examples discussed herein, the MDV RNA probes have the probe sequence appended to the 3' terminus of the mutant MDV sequence. Therefore, only the mutant MDV sequence is replicated upon the addition of Qβ replicase. The advantage of designing the MDV RNA probes in this fashion is that the probe sequence does not also need to be resistant to the inhibitory agent, since it is not replicated by Qβ replicase.

A real-time assay for monitoring the production of MDV RNA in a Qβ amplification system using the present probes and method is also the subject of the present invention. The agent used to reduce the replication of wild type MDV RNA also can be used in detecting the amplified product RNA (the product of the amplification process in which the mutant MDV RNA probe serves as the initial template). For example, the agent can be a dye, such as a fluorescent dye, which is used to detect the amplified product RNA. The fluorescence of some dyes, such as ethidium bromide and ethidium bromide homodimer, is enhanced upon binding to RNA, facilitating detection. In addition, despite the sequence differences which render it resistant to these dyes, the mutant MDV RNA also binds these dyes, and replication is only slightly slowed. This results in formation of a fluorescently-labelled mutant MDV RNA probe, the production of which can be followed in real time using fluorescence spectroscopy.

MDV probe constructs significantly increase the sensitivity, quantifiability and convenience of assay systems employing them. The present method allows the mutant MDV RNA probe to be selectively amplified in a Qβ replicase amplification system while simultaneously inhibiting the undesirable replication of any wild type MDV RNA which may be present. The detection or inhibitor reagent is generally a dye which binds to MDV RNA thereby increasing its fluorescence. Thus, the production of the mutant MDV RNA can be monitored by fluorescence spectroscopy in "real time" mode. (i.e., while the reaction is proceeding), providing a means for accurately quantitating the level of the target nucleic acids originally present in the sample.

BRIEF DESCRIPTION OF THE FIGURES

Figure 3:
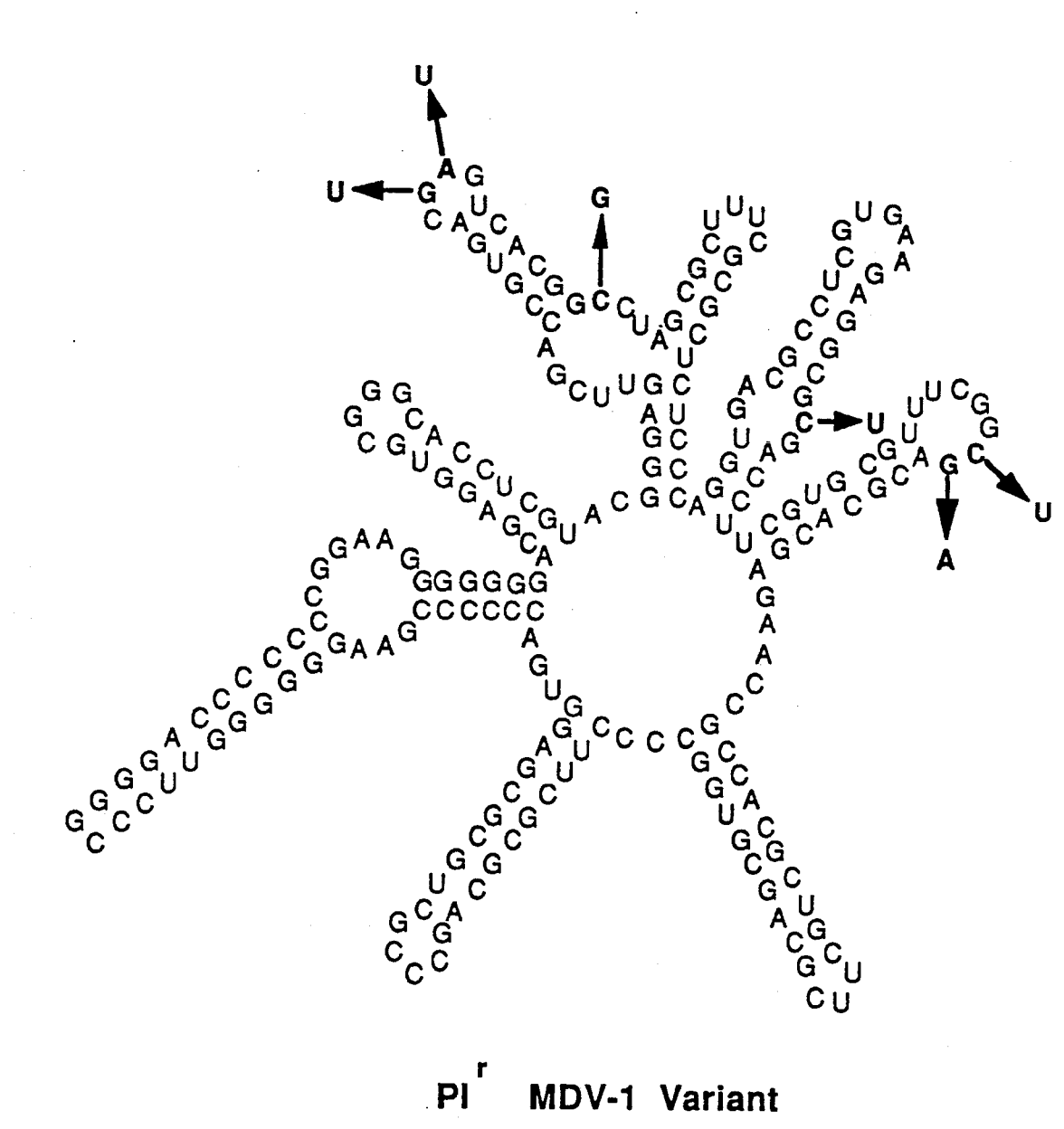

FIG. 3 is a schematic representation of the nucleotide sequence of a mutant, propidium-resistant (PI$^r$) MDV RNA. The altered (mutated) nucleotides are indicated in boldface type with arrows showing the alteration in the nucleotides.

FIGS. 5A and 5B show a schematic illustration of A) the nucleotide sequence of two oligonucleotides used in preparing mutant propidium iodide resistant MDV RNA clones; and B) a restriction map of the cloned sequence.

FIG. 6 is a schematic representation of MDV-SYN RNA. The mutated nucleotides are circled and boxed.

DETAILED DESCRIPTION OF THE INVENTION

Figure 1:
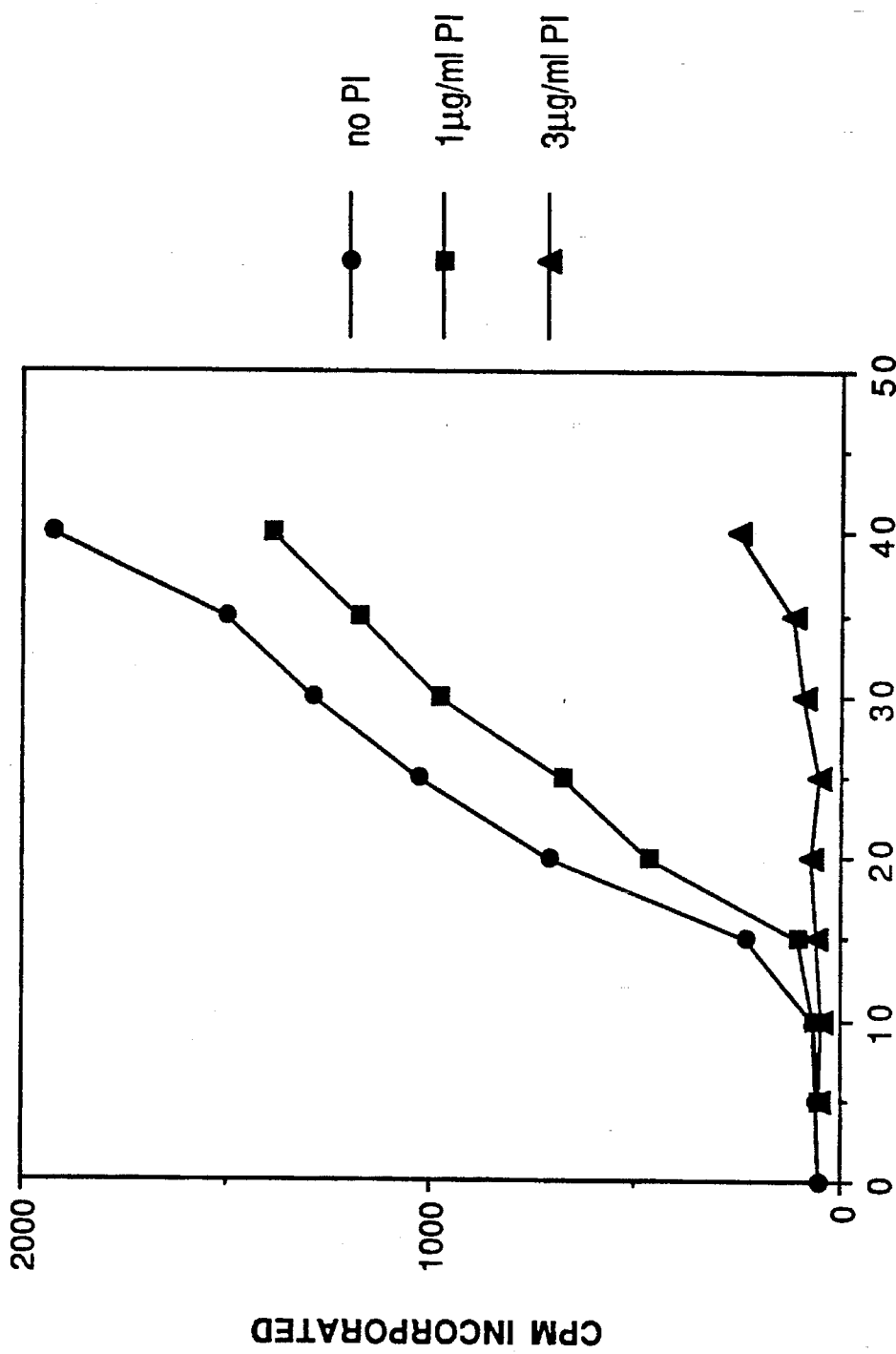
FIG. 1 is a graph illustrating the effect of propidium iodide (PI) on the rate of replication of wild type MDV-1 RNA.
Figure 2:
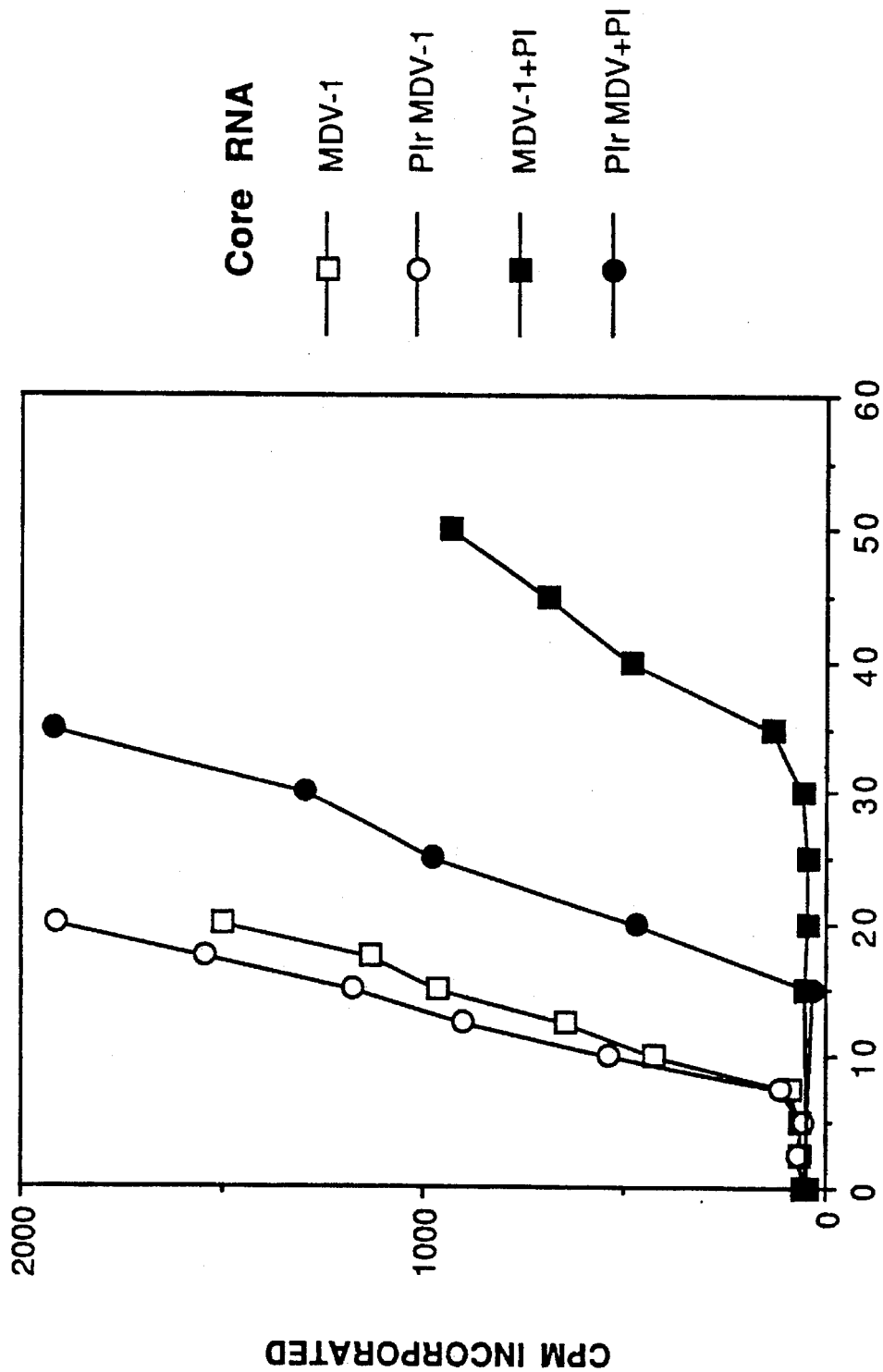
FIG. 2 is a graph illustrating the effect of propidium iodide (PI) on the rate of replication of wild type MDV-1 RNA and mutant, (propidium-resistant) (PI$^r$) MDV-1 RNA.

The present recombinant MDV RNA probes and method of amplifying them utilizes a mutant form of MDV RNA which is resistant to inhibition by agents which inhibit wild type, non-mutant MDV RNA. The nucleotide sequence of the mutant MDV RNA and the nucleotide sequence of the wild type MDV RNA differ in such a way that the mutant form is resistant to inhibition by agents which inhibit the replication of non-mutant MDV RNA. The term "wild-type" is used herein to describe naturally-occurring, endogenous midivariant RNA associated with Qβ replicase. The term "mutant MDV RNA" refers to MDV RNA which differs from wild type MDV RNA by at least one nucleotide. Ethidium-bromide-resistant mutant RNAs are described, for example, by Kramer et al., *J. Mol. Biol,* 89:719–736 (1974).

The mutant MDV RNA has two important characteristics: its replication is not inhibited by certain agents which inhibit replication of wild type MDV RNA, and it is a template for Qβ replicase. Mutant MDV RNA can be produced by exposing wild type MDV RNA to the inhibiting agent in a so-called evolution experiment (see Example 2). Alterations or mutations in the primary sequence of the wild type MDV RNA occur spontaneously in MDV RNAs which are passed through several rounds of replication in the presence of the inhibiting agent. Kramer et al., *J. Mol. Biol.,* 89:719–736

(1974). The presence of these mutations allows the template molecules bearing them to replicate faster, and eventually overtake the replication of non-mutated RNAs in the reaction. This "selection" process thus favors the replication of inhibitor resistant forms of the MDV RNAs.

The present recombinant MDV RNA probes are made by linking the mutant MDV RNA to the nucleic acid probe sequence of choice, for example by cloning, ligation or chemical coupling, to form a linked sequence (MDV RNA probe). The term "linking", as used herein, means that the nucleic acid sequence of choice is incorporated into or is attached to the 3' or 5' end of the MDV RNA nucleotide sequence. The term "nucleic acid probe sequence" refers to a nucleic acid sequence which is specific for a selected "target" nucleic sequence in a sample. The nucleic acid probe sequence is substantially complementary to, and hybridizes with, the target nucleic acid to form a hybridization complex. The hybridization complex can be isolated from the sample, the MDV-RNA probe released from the complex by standard techniques, and the MDV-RNA probe amplified by Qβ replicase.

These recombinant MDV RNA probes are used in a Qβ replicase amplification system in the present method. A Qβ replicase amplification system using an amplifiable probe is described generally, for example, by Chu et al.. *Nucleic Acids Research*, 14:449–603 (1986), and Lizardi et al. in *Biotechnology*, 6:1197–1202 (1988). These amplification systems rely on the ability of Qβ replicase to copy MDV RNA at a geometric rate, thereby producing a billion-fold increase in MDV RNA in about 30 minutes at about 37° C. The amplification by Qβ replicase allows for very sensitive and selective diagnostic assays. Such assays can be adapted for use in sensitive hybridization assays for viruses, bacteria, cancer and other genetic sequence-based tests. The present method makes it possible to selectively amplify specific MDV RNA probes, and simultaneously suppress the replication of wild type MDV RNA, thereby reducing background "noise" caused by the replication of wild type MDV RNA which may be present.

Agents which inhibit replication of wild type MDV RNA, and allow replication of mutant MDV RNA are used in the present method to permit selective amplification of the MDV RNA probes. These agents bind to the mutant MDV RNA but inhibit its replication much less than they inhibit replication of the wild type MDV RNA.

In the present method, one or more of these agents is added to the amplification system prior to or simultaneously with the mutant MDV RNA probes. Milli-molar amounts of the agent (in large excess of that required to bind to both the wild type MDV RNA and the mutant MDV RNA) is added. The agent binds to the wild type MDV RNA and the mutant MDV RNA, if present, but preferentially inhibits replication of the wild type MDV RNA.

Agents which selectively inhibit the wild type MDV RNA include ethidium bromide, ethidium bromide homodimer, propidium iodide, proflavine, quinacrine, Hoescht 33258 (bis-benzamidine), dimidium bromide and acridine orange. Dyes such as ethidium bromide, ethidium bromide homodimer and propidium iodide are particularly useful inhibiting agents. These dyes, in addition to inhibiting replication of wild type RNA, are fluorescent. Their fluorescence increases upon binding to nucleic acids, such as MDV RNA. Thus, mutant MDV RNA binds the dye which increases its fluorescence and, thus, can be detected using fluorescence spectroscopy. Due to the faster replication rate of the mutant MDV RNA under these conditions a single molecule added to the reaction will yield the mutant RNA, as it effectively outcompetes the wild type MDV RNA for Qβ replicase and is the predominant product of the Qβ replicase reaction, even in the presence of about 100 to about 1000 molecules of contaminating wild type MDV RNA. The fluorescence properties of the dye allows the production of the mutant MDV RNA probes to be followed as it proceeds, that is, a real-time assay is possible using the present method. Other labelling methods (e.g., $^{32}P$, biotinylated, sulfonated or 5-bromo UTP, etc.) which do not rely on the fluorescence properties of these inhibitory dyes also can be used as a means of detecting these RNAs.

Quantitative assays having reduced background noise due to the suppression of replication of the wild type MDV RNA are also the subject of the present invention. The assays can be used to quantitate the amount of mutant MDV RNA which is produced by the amplification process and, therefore, also the initial amount of a target nucleic acid which was originally present in a sample. In this assay method, amplifiable hybridization probe sequences which are specific for or complementary to the target nucleic acid, are linked to or inserted into the mutant MDV RNA, e.g., by cloning, ligation or chemical coupling. The nucleic acid sequences do not have to be one hundred percent complementary to the target sequences, but sufficiently complementary to bind to or hybridize with the target sequences under the hybridization conditions used. The mutant MDV RNA probe is then contacted with a test sample under hybridization conditions thereby forming probe-target complexes. The probe-target complexes are isolated by standard techniques, such as reversible target capture. Hunsaker et al., *Analytical Biochem.* 181:360 (1989). The probes are then released from their targets and amplified by incubation with Qβ replicase. The Qβ replicase copies the probes, and the number of probes increases in a geometric manner. That is, after each round of copying, the number of RNA molecules doubles. The amount of target initially present in the sample then can be calculated from the amount of time required to synthesize a particular amount of RNA. For example, the replication kinetics of assays prepared with known amounts of target molecules can be used to develop standard curves. The smaller the number of original targets present in the sample, the longer it takes to synthesize a particular amount of RNA. In the present assay method, by using mutant MDV RNA probes as the template, the replication of wild type MDV RNA contaminants can be suppressed, allowing selective replication of the mutant MDV RNA probes. The present method provides a simple, accurate, sensitive assay method with reduced background noise.

An important manifestation of the present method is that it enables the real-time detection of product in Qβ replicase amplification systems. That is, the actual progress of the reaction can be monitored as it occurs rather than by adding a detectable label to determine the amount of product produced after the reaction is completed. Real-time detection allows the kinetics of the reaction to be monitored and the precise time at which the RNA product emerges from the geometric phase of replication to be determined. This latter measurement is the most reliable measure of the initial level of target RNA. Lizardi et al., *Biotechnology* 6:1197–1202 (1988). Thus, a convenient, accurate and reproducable means of quantitating the initial amount of target is available.

In one embodiment of the present method, termed a homogeneous fluorescence rate measurement, dyes are used which are capable of binding with the replication products of the Qβ replicase enzyme, wild type MDV RNA, and mutant MDV RNA, to continuously monitor the synthesis of product RNA. A fluorimeter can be used which accurately controls temperature and allows the reaction to occur in a completely sealed environment, and allows the reaction to be followed. In this method, one or more fluorescent dyes is added at the start of the reaction along with buffer, nucleoside triphosphates and the Qβ replicase enzyme. Qβ replicase is initially added at a concentration which is greater than the concentration of template MDV RNA. The concentration of dye at the start of the reaction is also significantly greater than the initial concentration of template. The concentration of amplified RNA increases geometrically in time. When the concentration of RNA increases above approximately 0.1 μM, it reaches a point where RNA binds enough dye to result in an easily measurable increase in the fluorescence. The fluorescence is monitored as a function of time and the time at which an increase in the fluorescence is first detected (response time) is determined. The response time is inversely related to the logarithm of the initial concentration of template molecules. Lizardi et al., *Biotechnology* 6:1197–1202 (1988); Lomell et al., *Clinical Chemistry*, 35 :1826–1831 (1989).

Standard curves can be prepared using purified MDV probe molecules as in Example 4, using purified target molecules as in Example 5, or purified target organisms as in Example 6, as most appropriate for specific applications.

The present method of monitoring Qβ replicase reactions is easy to manufacture, is more accurate than end-point measurements, requires simple instrumentation, can discriminate between different types of replicable molecules based upon their response profile, is inexpensive and permits quantitative evaluation of initial MDV RNA and target nucleic acid concentrations.

The invention will now be further illustrated by the following Examples, which are not intended to be limiting in any way.

EXAMPLES

Example 1

Inhibition of MDV-1 Growth by Propidium Iodide

Preparations of Qβ replicase prepared by the procedure of Eoyang & August typically contain between 100 and 10,000 molecules of MDV-1 RNA per microgram of protein. Eoyang and August, *Proc. Nucl. Acids Res.*, 2:829–839 (1972). This "wild type" RNA replicates and generates a signal even when exogenous template RNA is omitted from the reaction.

A number of dyes, including ethidium bromide, ethidium bromide homodimer, propidium iodide, proflavine, quinacrine, Hoescht 33258 (bis-benzamidine), dimidium bromide and acridine orange, were tested for their ability to inhibit the replication of MDV-1 in linear-phase reactions, i.e., where the template RNA is present in excess over the enzyme and the amount of replicated RNA thus increases linearly with time. All of the dyes listed above, except Hoescht 33258, inhibited the replication of MDV-1 by Qβ replicase. One of the strongest inhibitors, propidium iodide, was selected for further study. A concentration of dye producing a 70% inhibition of replication, about 3μg/ml, is sufficiently low to allow detection of the fluorescence increase produced when the dye binds to the RNA products of the reaction.

Propidium iodide was tested for its effect on the replication of wild type RNA in a preparation of Qβ replicase. Propidium iodide in an amount of either 0, 1, or 3 μg/ml was added to a reaction buffer containing: 90 mM Tris HCl (pH7.5), 14 mM $MgCl_2$, 0.4 mM each ATP, GTP, UTP, and CTP, and 10 μCi α-$^{32}$P-CTP. The Qβ replicase reaction was initiated in each sample by addition of 1.2 μg of Qβ replicase prepared according to the method of Eoyang and August, (1972), ibid. Aliquots of the reaction mixture were withdrawn every 5 minutes and spotted on DE81 filters (Schleicher & Schuell Inc., Keene, N.H.). The spotted filters were washed repeatedly with 0.5M $NaPO_4$, (pH7.0) to remove unincorporated nucleotide. The filters were counted for Cerenkov radiation by standard procedures in a scintillation counter. The results are shown in FIG. 1. Addition of propidium iodide delayed the point in time at which levels of incorporation resulting from the replication of wild type MDV-1 template became detectable. One microgram per milliter delayed the appearance of replicated product between about 2–5 minutes, which corresponds to about 20–50% inhibition of the rate of replication in the geometric phase, and 3μg/ml delayed the appearance of product for about 20 minutes, which corresponds to approximately a 3-fold reduction in the rate of replication.

Example 2

Generation and Analysis of a Propidium-Resistant RNA Template for Qβ Replicase In order to obtain a propidium-iodide-resistant mutant RNA, an "evolution" experiment was carried out, starting with unmodified MDV-1. MDV-1 was serially diluted in water $10^8$-fold to a final concentration of approximately $10^4$ RNA molecules/μl. Five microliters of the diluted RNA was added to a Qβ replicase reaction as described in Example 1, except that propidium iodide was present at a concentration of 1.5 μg/ml. After 20 minutes, the reaction was stopped by adding EDTA to a concentration of 25 mM. The reaction product was serially diluted $10^8$-fold, and that dilution added to a second, fresh Qβ replicase reaction containing 1.5 μg/ml propidium iodide. This process was repeated for a total of 12 serial reactions. Separate time courses indicated that the MDV-RNAs in the last of the reactions showed faster rates of replication in the presence of propidium iodide than those present early in the selection process. For example, $10^4$ molecules from the third serial reaction required about 14 minutes to reach detectable levels in the reaction, whereas the same amount of template RNA obtained from the 12th serial selection reaction required less than 10 minutes to attain the same level.

For analysis of the evolved mutant MDV-1 RNAs, cDNAs of the product RNA(s) first were obtained. The (+) and (–) strands of the replicated RNA product were first separated by the following procedure: the reaction products (a mixture of both plus and minus strands) were precipitated with ethanol and redissolved in 95% formamide. The solution was heated to 90° C. for 2 minutes and chilled on ice to denature the strands, which were then resolved by electrophoresis through an 8% polyacrylamide gel (containing 50 mM Tris-borate [pH8.3] and 3 mM $MgCl_2$) at 12.5 V/cm, overnight at 4° C. The separated (+) and (–) strands were visualized by autoradiography, the gel slices containing them were excised, and the RNA was eluted overnight in 0.5M $NH_4OAc$, 1 mM EDTA, 0.1% SDS. The RNA was then concentrated and collected by ethanol precipitation. In parallel, non-mutated MDV-1 was also strand separated as a control. One picomole aliquots of each of the faster migrating RNA species (the (–) minus strand) were separately annealed to 5 pmol of a DNA primer oligonucleotide having the sequence: 5' -CCCGACGTCTTTAATACGACTCAC-TATAGGGCCCTCTTCCG-GGGACCCCCCCG-GAAGGGGGGACGAG- 3' by heating to 90° C. in 50 µl of a solution containing 0.1M Tris (pH8.5) and 20 mM KCl, followed by slow cooling to 55° C. Five µl of a mixture containing 2 mM each of dATP, dGTP, dCTP, and TTP in 0.1M $MgCl_2$ and 10 mM dithiothreitol, and 2 units of avian myoblastosis virus reverse transcriptase (Seikagaku) were added to the annealed RNA/primer mixture and the reactions incubated for 30 minutes at 55° C.

Double-stranded cDNAs were obtained by polymerase chain reaction (PCR) from each of the above products. In this process, 5 µl of the reverse transcriptase reaction products were added to separate 100 µl mixtures containing 10 mM Tris HCl pH8.5, 0.05M KCl, 10 mM $MgCl_2$, 0.01% gelatin, 200 µM each dATP, dGTP, dCTP, and TTP, 5 µCi α-32P-dATP, 100 pmol of the DNA oligonucleottde above, 100 pmol of a DNA oltgonucleotide have the sequence 5'-CTGTTTAAAAGGATCCCGGGAAC-CCCCCTTCGGGGGGTC-3', and 5 units of *Thermus aquaticus* (Taq) DNA polymerase (U.S. Biochemicals). The mixtures were heated to 94° C. for 2 minutes, cooled over 5 minutes to 68° C., incubated for 10 minutes at 68° C., and returned to 94° C. to initiate the second round. This thermal cycle was repeated 25 times. The products of the reaction were ethanol precipitated, resolved on a non-denaturing 6% polyacrylamide gel and recovered from the gel by standard elution methods, as described above. The products of these reactions were double stranded cDNAs of the mutant or control MDV-1 RNAs which have appended to one terminus a promoter site for T7 RNA polymerase.

Each purified PCR product was transcribed in a reaction containing 0.04M TrisHCl (pH8.5), 5 mM $MgCl_2$, 5 mM DTT, 0.5 pmol PCR product and 70 units T7 RNA polymerase (Pharmacia) for 1 hour at 37° C. The product RNAs were plus strands of the original MDV-1 or variant RNAs used to prime the initial reverse transcriptase reactions. In addition, each product RNA bears a 12 nucleotide extension appended to the normal MDV-1 5' terminus (of sequence 5'-pppGGGCCCUCUUCC-3') and a 17-nucleotide extension appended to the 3' terminus (5'-GGGAUCCUU-UUAAACAG3') These RNA plus strand products were resolved on a 6% polyacrylamide gel containing 8.3M urea, and recovered as described above.

To verify that the mutations conferring resistance to propidium iodide were largely contained within that portion of the RNA not complementary to the PCR primers, $10^5$ of each of the transcripts from the PCR products were replicated in reactions either lacking or containing 3 μg/ml propidium iodide. The reactions were monitored as described in Example 1. The results are shown in FIG. 2. In the absence of propidium iodide, both the RNA generated from the unmodified MDV-1 RNA ("Core RNA=MDV-1") and that generated from the propidium-resistant variant ("Core RNA=$PI^r$ MDV-1") showed nearly identical replication rates, each appearing at between about 7–7.5 minutes in the reaction (the point at which the linear increase in incorporation would intercept the abscissa by extrapolation). In contrast, in the presence of propidium iodide ("MDV-1+PI"), the resistant mutant RNA appeared in 15 minutes but the non-mutant RNA derived from the unmodified MDV-1 required 33–34 minutes to replicate to detectable levels. These results indicate that the sequence changes produced in the mutant RNA molecule do not affect its replication under "nonselective" conditions (i.e., in the absence of propidium iodide), and that the changes confer an increased ability to replicate in the presence of the dye.

Each of the PCR products obtained above were sequenced by generation of single-stranded template DNAs by "asymmetric" PCR. Innis, et al., *PNAS,* 85:9436–41 (1988). Sequencing was performed by employing Taq DNA polymerase and the primer oligonucleotides used above. In order to reduce "band compressions", dGTP in the reactions was replaced with a 3:1 mixture of 7-deaza dGTP:dGTP. The sequence changes observed are shown schematically in FIG. 3.

Example 3

Detectability of Mutant Propidium-Resistant RNAs in the Presence of Propidium Iodide The mutant RNAs obtained in Example 2 were examined to determine the effect of propidium iodide on the lowest level of probe which is capable of yielding detectable amounts of RNA in a Qβ replicase reaction. Generally, probes produced by appending sequence elements to either the 3' or 5' termini of an MDV RNA require larger numbers of probe molecules to be added to the reaction in order to obtain an exponential amplification and ultimately yield products detectable by fluorescence or incorporation of labelled nucleotides. (See, Stefano, U.S. Ser. No. 370,218, filed Jun. 22, 1989, the teachings of which are incorporated herein by reference).

The effect of propidium iodide on the limiting number of probes detectable by Qβ replication was assessed by initiating Qβ replicase amplification reactions with various amounts of the RNAs obtained via transcription of the PCR products obtained in Example 2. Two reaction sets were run: one lacking propidum iodide, the other containing 2 μg/ml of the dye. The reactions were stopped after 30 minutes (for reactions lacking the dye) or 60 minutes (for reactions containing dye), by addition of EDTA and the propidium iodide concentration was brought to a final concentration of 3 μg/ml in all of the samples. The presence of replicated RNA was determined by the fluorescence resulting from binding of propidium iodide to the RNA, which was detected by placing the reactions in a microtiter dish and placing it over a 365 nm ultraviolet light source. In the absence of propidium iodide, $10^2$–$10^3$ molecules of the non-resistant species of RNA (e.g., the control) were required to be present initially to eventually yield detectable levels of product. However, when propidium iodide was present during replication, $10^4$ molecules were required. With the propidium-iodide resistant variant RNA (mutant RNA), $10^3$ probe molecules were detectable irrespective of the presence of propidium iodide during the Qβ reaction. This indicates that the sequence changes in the mutant RNA increased its rate of replication in the presence of propidium iodide relative to its non-resistant "parent" MDV-1, and also decreased the number of probes required to produce a detectable signal relative to a non-resistant MDV when replicated in the presence of the dye.

Example 4

Preparation of Propidium Iodide Resistant Probes by Cloning

Propidium iodide resistant MDV RNA molecules are not inherently probes. Rather, the MDV moiety serves as the detection ligand. As discussed in the background section above, MDV detection probes also must contain a portion of sequence which permits them to specifically hybridize to a target nucleic acid. Such probe sequences can be inserted internally in MDV molecules (Lizardi et al., (1988) *Biotechnology*, 6:1197–1202, or they can be appended to either the 5' or 3' terminus of the MDV molecule (Chu et al., *Nucleic Acids Research*, 14:559–603 (1986); Stefano U.S. Ser. No. 370,218 ibid.). A rapid, convenient and accurate means of constructing such dye resistant probe molecules is desirable.

One such means can be derived from the procedure described in Example 3; namely, use of the polymerase chain reaction (PCR) to copy a dye resistant MDV RNA while simultaneously appending extra sequences on the termini of the cDNA product. For example, a T7 RNA polymerase promoter could be appended to the 5' terminus and a specific probe sequence could be appended to the 3' terminus.

```
T7          MDV                        probe
----+-----------------------------+------
| | | | | | | | | | | | | | | | | | | | | | | | |
----+-----------------------------+------
                 V
                 V (+ T7 RNA polymerase)
                 V
                 V
           MDV                        probe
           _____|_____
```

Transcription using T7 RNA polymerase would yield the correct MDV probe construct.

Alternatively, a more "classical" cloning procedure can be employed, as described below.

The propidium-iodide resistant MDV RNA probes described in Examples 5 and 6 were prepared by cloning the probe sequences into specialized transcription plasmids which have been designated MDV-SYN vectors. The MDV-SYN vectors are a series of plasmids designed to allow easy cloning of target-specific probe sequences, and subsequent production of MDV RNA probe molecules, which can replicate in the presence of at least 3.2 µg/ml of propidium iodide. In addition, the MDV-SYN plasmids facilitate the production of these propidium iodide-resistant MDV RNA molecules with probe sequences added onto the 5' end, added to the 3' end, inserted within the RNA, or any combination of these three positions through sequential cloning experiments.

Figure 4A:
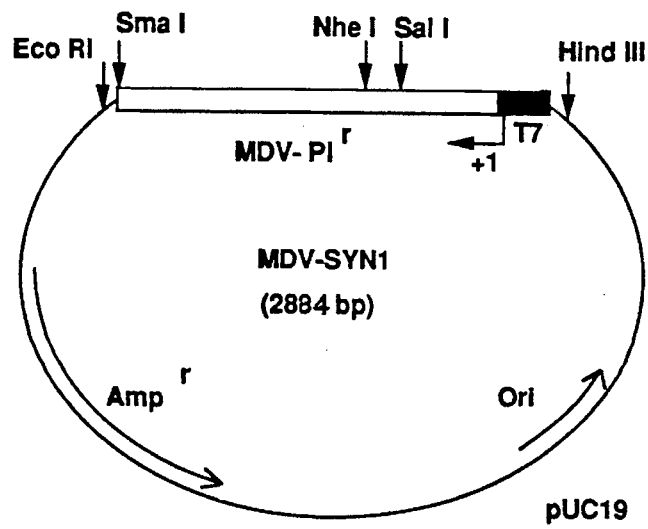
FIG. 4A, 4B and 4C represent three plasmids, MDV-SYN1, MDV-SYN2 and MDV-SYN3, used in cloning mutant propidium-iodide resistant probes.
Figure 4B:
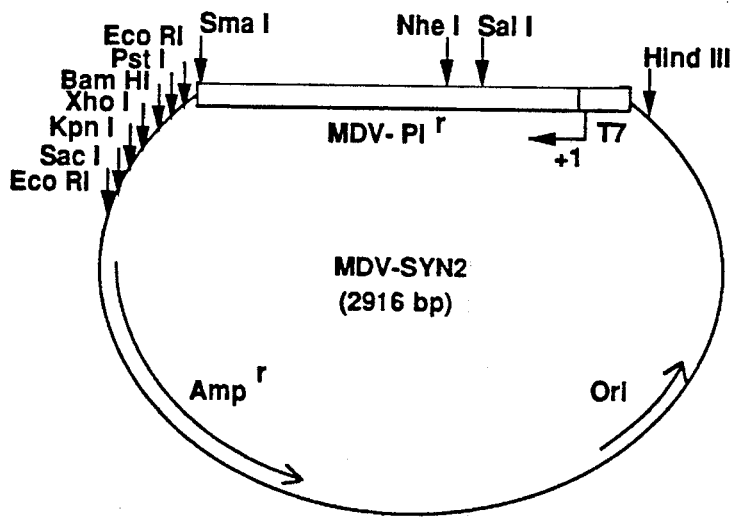
Figure 4C:
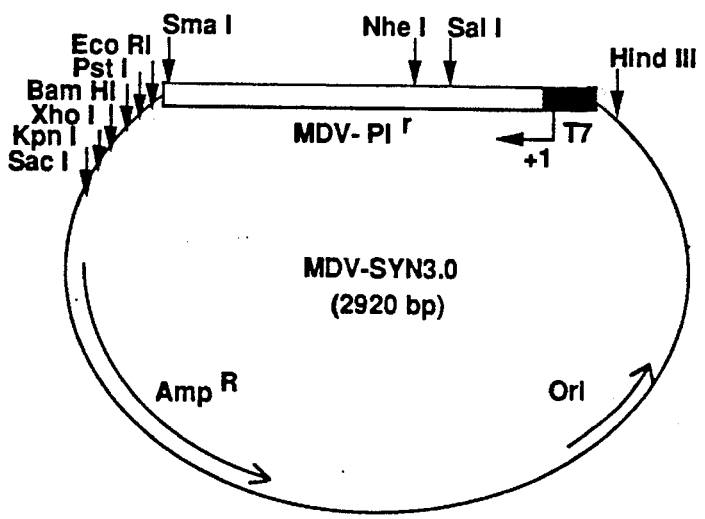

Three MDV-SYN vectors were created which differ from one another only in the region of the multiple cloning site. The three vectors are shown schematically in FIG. 4. Following the MDV RNA coding sequence, MDV-SYN1 contains Sma I and Eco RI sites. MDV-SYN2 contains Sma I, Eco RI, Pst I, Bam HI, Xho I, Kpn I, and Sac I sites and another Eco RI site. MDV-SYN3 is identical to MDV-SYN2 except it does not contain the Eco RI site that is furthest from the MDV RNA sequence.

Figure 5A:
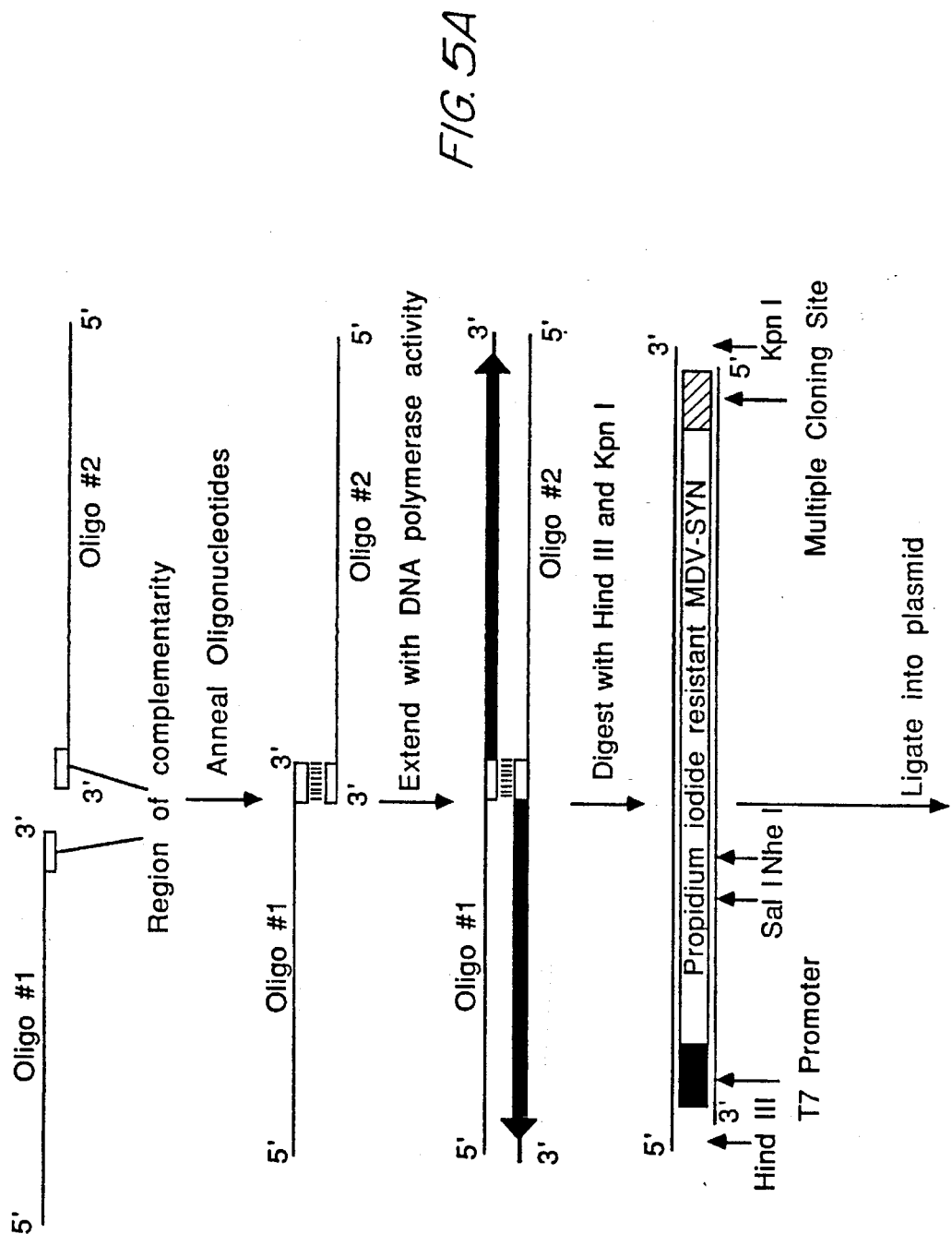

The MDV-SYN vectors were constructed from two parts. The first part was simply the plasmid pUC19 which provides all the plasmid functions such as replication and drug resistance. The second part was derived from two overlapping synthetic oligonucleotides. The sequence of the two oltgonucleotides used and a diagram of how they were used to produce the MDV-SYN vectors is shown in FIGS. 5A and B. The portion of the oligonucleotide seqences which encodes the propidium iodide resistant MDV RNA was derived (with one nucleotide in exception to create the Sal I site) from the nucleotide sequence of the mutant MDV RNA (called MDV-PI') which was isolated through multiple rounds of selective replication in the presence of propidium iodide as described in Example 2. The sequence of the MDV-SYN RNA is chemically synthesized and, therefore, exactly defined. MDV-SYN RNA and MDV-PI' RNA replicate with nearly identical kinetics in the presence of propidium iodide.

Figure 10A:
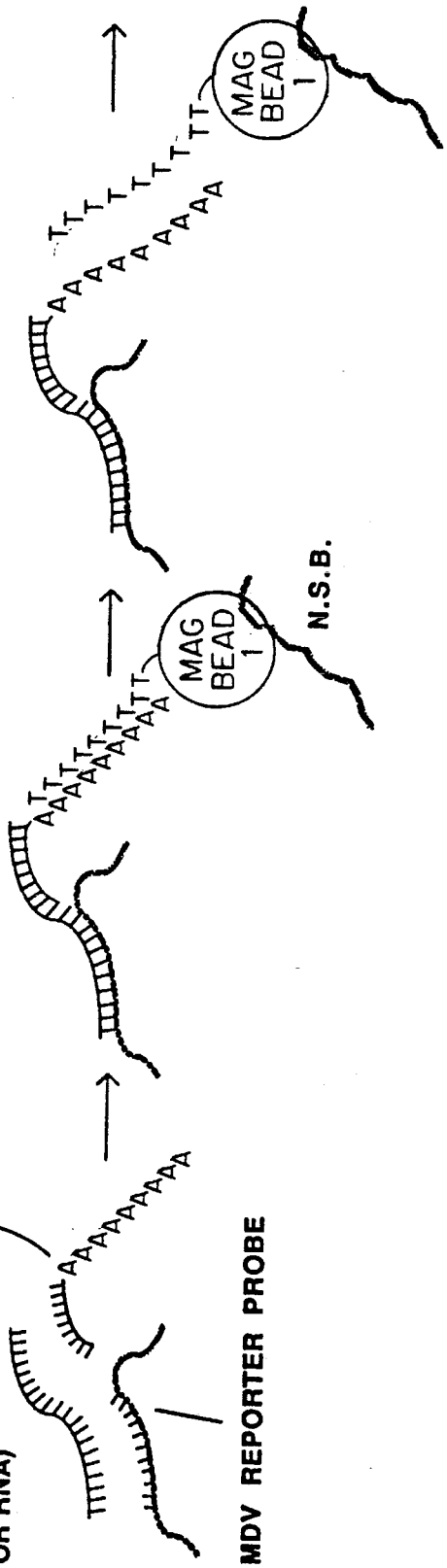
FIGS. 10A and 10B represent the reversible target capture assay process with subsequent amplification of the MDV detector probe by Qβ replicase.
Figure 10B:
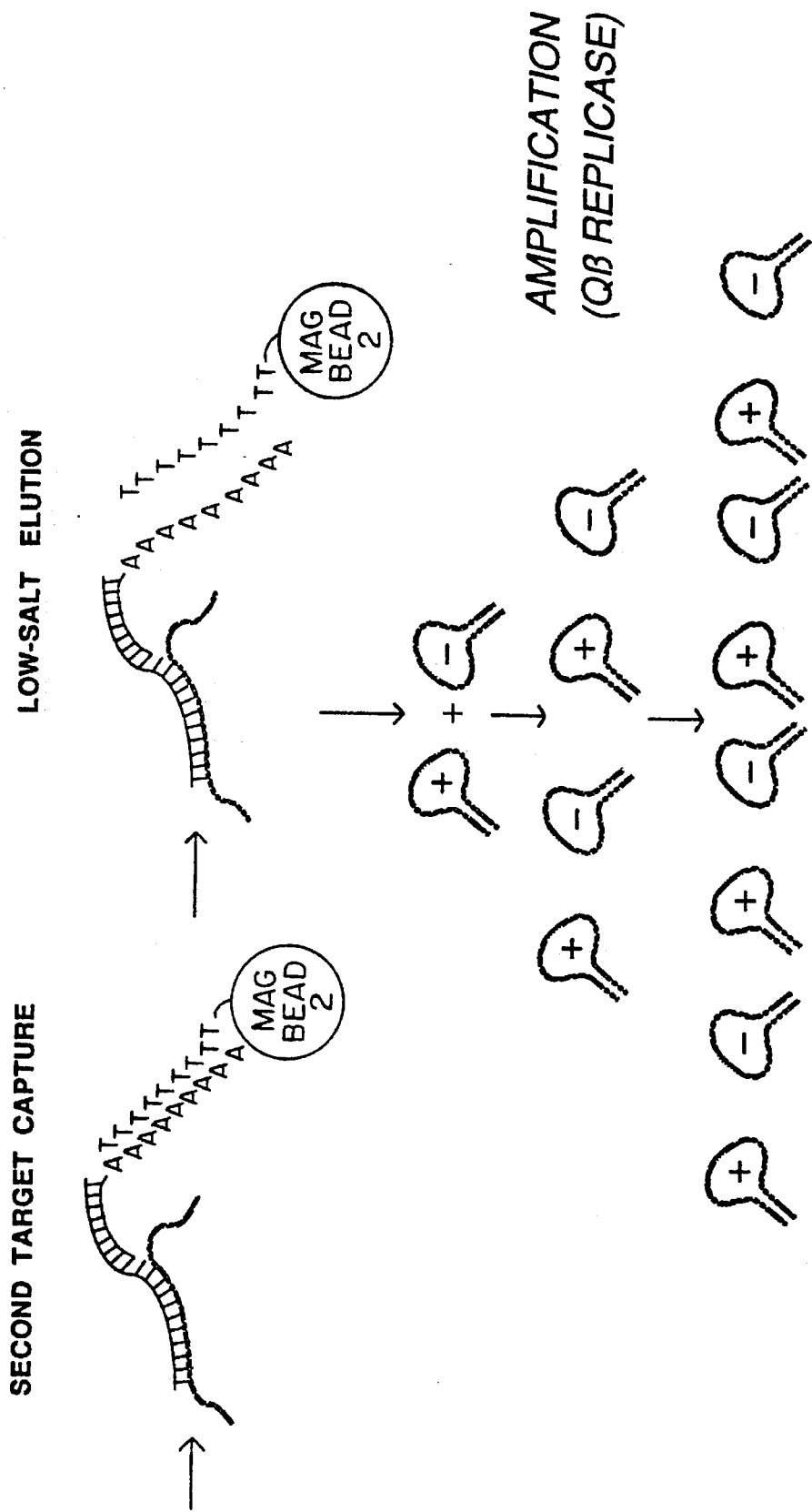

The sequence of the MDV RNA molecules produced by transcription with T7 RNA polymerase of Sma I restricted MDV-SYN plasmids is shown schematically in FIG. 10. The five nucleotides that were identified in MDV-PI' (Example 2) as those responsible for conferring resistance to propidium iodide are circled in the MDV-SYN RNA sequence in FIG. 6. These are U63, U64, U117, U136, and A137. The underlined residue, G72, is present in some, but not all, naturally occurring MDV-1 RNA variants. The G72 residue in the DNA sequence forms the first nucleotide of the recognition sequence G-C-T-A-G-C for the restriction enzyme Nhe I. The Nhe I restriction site is unique (i.e., appears only once) in MDV-SYN vectors. The boxed G nucleotide, G51 differs from all other known MDV-1 RNAs (they contain a U51) and was introduced into the MDV-SYN vectors to create the unique Sal I site, G(51)-T-C-G-A-C. The unique Sal I and Nhe I sites flank a region of MDV known to accept additional sequences with minimal affects on replication and therefore are useful sites for insertion of probe sequences within the body of the MDV-SYN RNAs.

Figure 6:
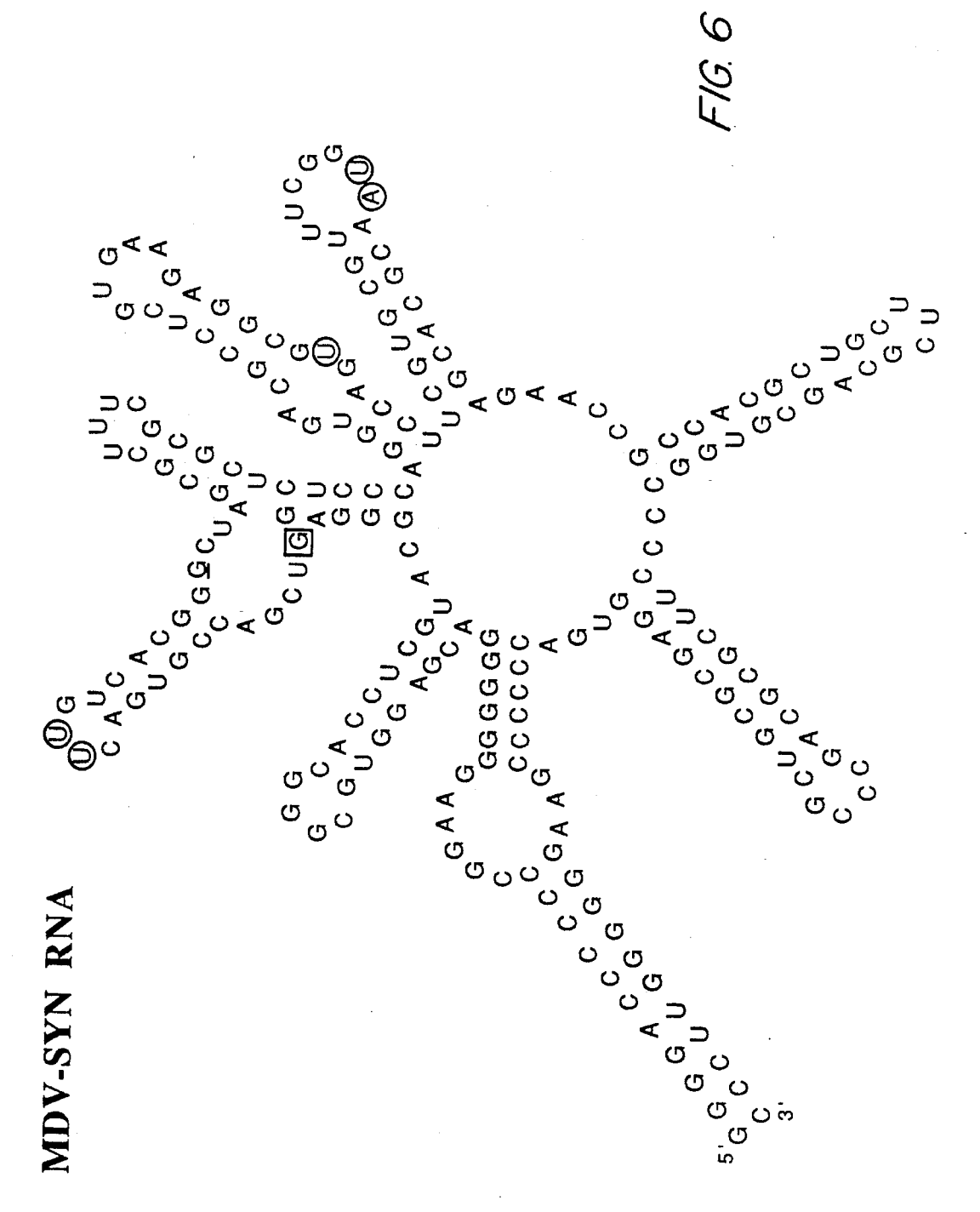

MDV-SYN2 was constructed initially; MDV-SYN1 and MDV-SYN3 were derived from it as described below. The two oltgonucleotides (shown in FIG. 5A) were annealed to each other through hybridization of a twelve base complementary region at the 3' end of each oligonucleotide. This was accomplished by mixing the two oligonucletides together in 10 mM Tris (pH 8.5), 50 mM KCl, 3 mM MgCl$_2$, 0.109 gelatine and 1 mM dNTPs, heating to 94° C., and cooling to 60° C. to promote hybridization. The 3' ends of each were extended with Taq DNA polymerase at 70° C., using the 3' end of one oltgonucleotide as a primer for synthesizing the complementary sequence of the other oligonucleotide template. Twenty cycles of heating, cooling and extension (PCR) were performed. The full length ds DNA products were purified from a 5% polyacrylamide gel as described previously and the ends filled with the Klenow DNA polymerase. These molecules were restricted with the enzymes Hind III and Kpn I to create ends with four base single stranded overhangs. The products were again gel purified (1.4% agarose gel) and then were ligated into the pUC19 plasmid, which had also been doubly restricted with Hind III and Kpn I to create complementary four base overhangs to accept the restricted, extended oligonucleotides. Finally, the ligated material was introduced into *E. coli* strain DH5alpha (BRL) and the resulting colonies screened for proper recombinant molecules. MDV-SYN1 was derived from MDV-SYN2 by deleting the small fragment between the two Eco RI sites of MDV-SYN1 (FIG. 6). MDV-SYN3 was produced by isolating the HindIII/Kpn I fragment from MDV-SYN2 (containing the T7 promoter and MDV RNA coding region) and ligating it into the complementary restriction sites in a pUC19 plasmid which lacked an Eco RI site.

Figure 7:
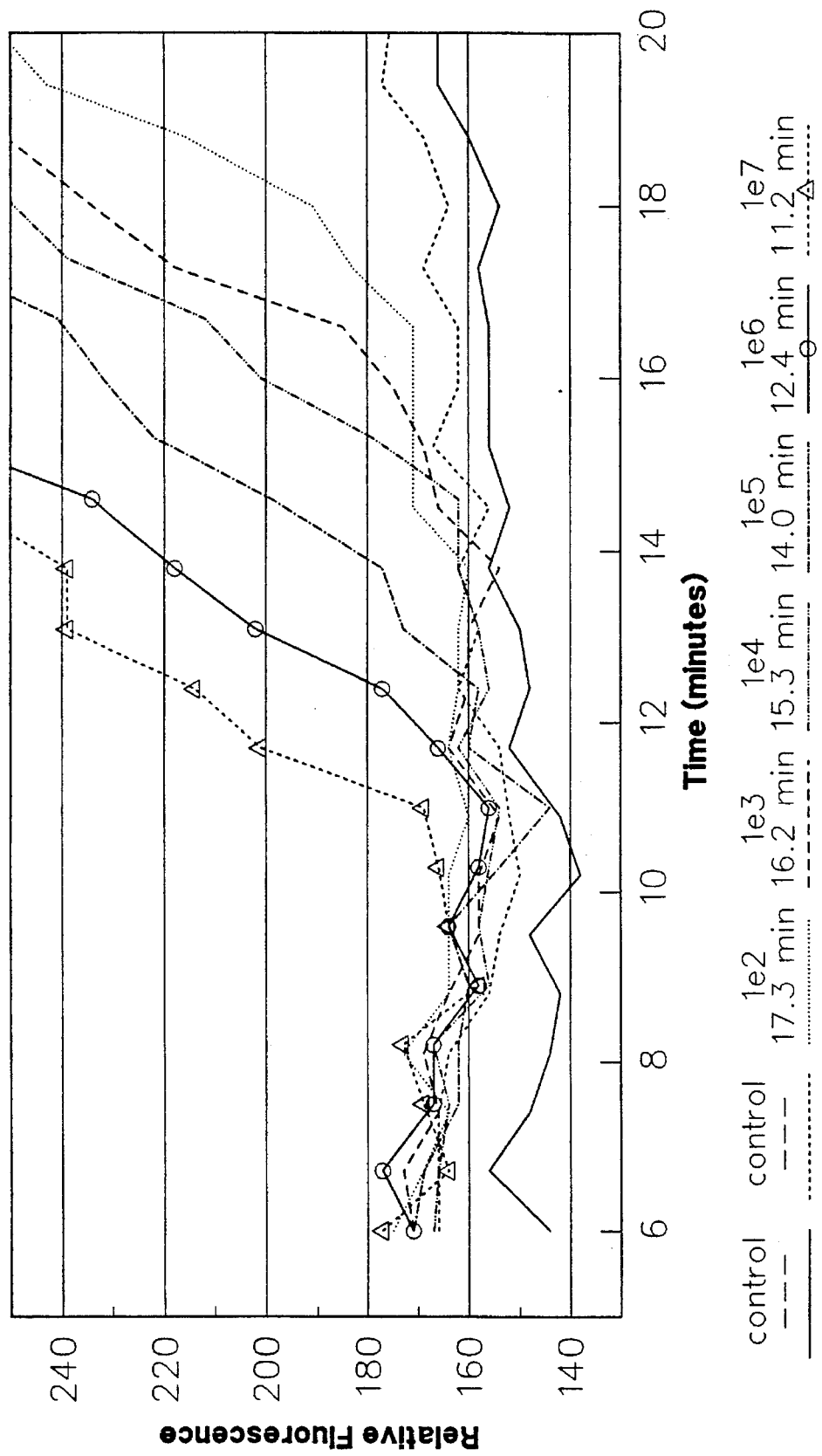
FIG. 7 is a graph illustrating the results of a real time detection of the amplification by Qβ replicase of MDV-SYN3 RNA.

An analysis of the replication properties of MDV-SYN RNA is shown in FIG. 7. In this experiment, MDV-SYN3 was restricted with Sma I, transcribed with T7 RNA polymerase and the resulting RNA purified by gel electrophoresis. Various amounts of the MDV-SYN3 RNA (log increments from 100 to 10,000,000 molecules) were then replicated by Qβ replicase in the presence of 3.2 µg/ml propidium iodide according to the procedure described in Example 3. The replication rate was measured for each RNA concentration in real time by measuring the accumulation of RNA through the fluorescence generated by the association of propidium iodide with the product RNA as detected by the Fluoroskan-II fluorometer (Flow Laboratories). As shown in FIG. 7, 100 molecules can easily be detected by this approach. Appearance of fluorescence above background differs by approximately one minute for each 10-fold dilution of the input MDV-SYN RNA molecules.

Example 5

Method for Reversible Target Capture Assay for Human Immunodeficiency Virus Using Qβ Amplification of Propidium Iodide Resistant Probes The experimental samples were t-lymphoblastoid cells prepared from blood of HIV negative donors by the method of Carter et al. in *Lancet,* (June 6):1286 (1987). These were lysed using a buffer containing 5M guanidine thiocyanate (GuSCN), 0.1M EDTA (pH 7.0), and 10% dextran sulfate. Some samples were spiked with a synthetic target RNA. This RNA was generated by transcription of a cloned fragment of the pol region of an HIV-1 provirus with SP6 polymerase as described by Pellegrino et al. in *Biotechniques* 5:452 (1987).

Figure 8:
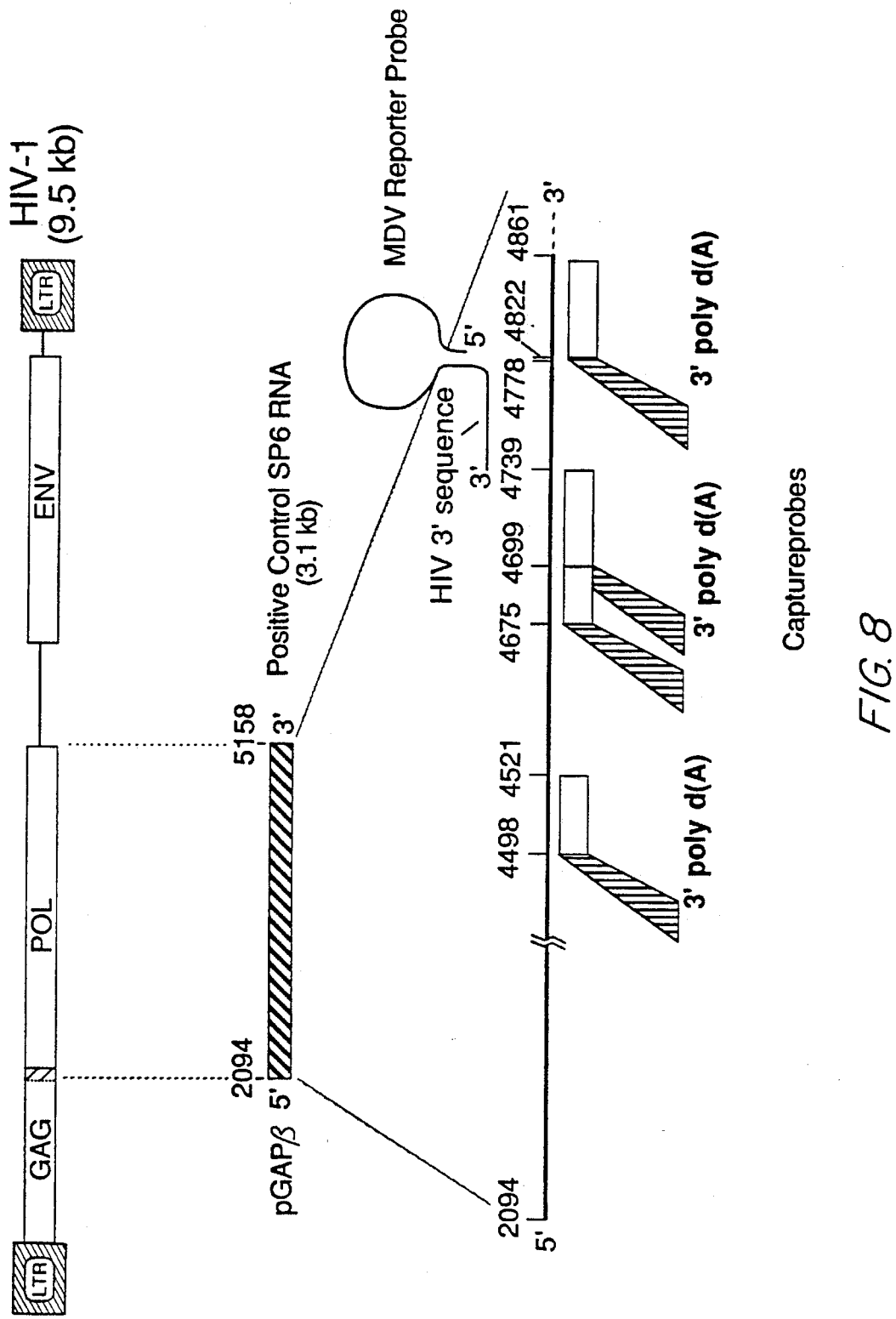
FIG. 8 is a schematic representation of the HIV genome showing the approximate location of the target sites of the capture probes and detector probes used in the reversible target capture assay for HIV of Example 5.

Capture probes were bifunctional DNA molecules containing a short (40 nucleotide) target-specific portion and a long (approximately 150 nucleotide) polyadenostne (dA) "tail" appended to the 3' terminus. The target specific portion was prepared by standard β cyanoethyl phosphoramidite chemistry on a 380A synthesizer. (Applied Biosystems, Foster City, Calif.). The dA tail was appended by a standard terminal deoxynucleotidyl transferase protocol. Nelson and Brutlag, *Methods in Enzymology* 68:41 (1979). Four capture probes were used. These were designated 1157, 1149, 839 and 1196 (FIG. 8).

Figure 9:
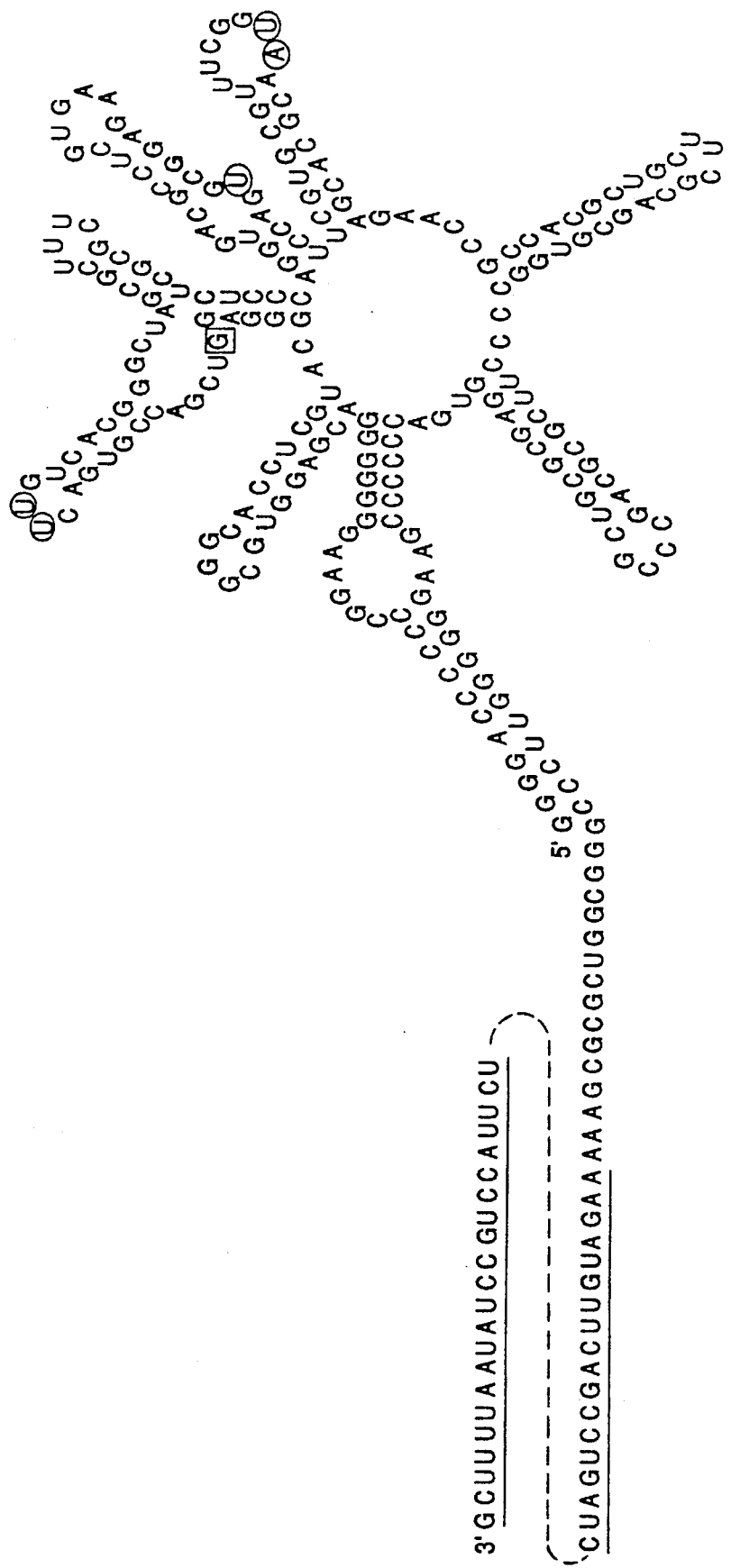
FIG. 9 is a schematic representation of an HIV-specific MDV RNA probe, which contains an internal insert and a 3' extension specific for HIV RNA, which is capable of being replicated by Qβ replicase.

The detector probes used for these assays were recombinant molecules of propidium-iodide resistant MDV RNA with extensions of approximately 40 nucleotides on their 3' ends. These extensions constituted the probe moiety of the MDV probe molecule and were complementary to a region of the target nucleic acid. The MDV RNA probes were prepared by inserting oligonucleotides containing the probe sequence into the MDV-SYN2 plasmid transcription vector (see Example 4) which contained: a T7 RNA polymerase promoter site, a copy of a propidium iodide resistant MDV, and a cloning site for insertion of probe oligonucleotides, in that order. Following purification of the recombinant plasmid and cutting with the appropriate restriction endonuclease (in this case EcoRI), MDV RNA probes of the correct configuration are produced by transcription with T7 RNA polymerase. The RNA products were purified by polyacrylamide gel electrophoresis and quantitated by standard spectrophotometric methods by following the incorporation of a radioactive label during the transcription. The nucleotide sequence of the HIV-specific MDV RNA probe is shown schematically in FIG. 9.

Capture probes (10 μg/ml) and detector probe (4 ng/ml) were added to each sample and the mixture was incubated at 37° C. for 30 minutes to allow hybridization to occur. Hybrid complexes between the target nucleic acids, capture probes and MDV detector probes formed after addition of the probes to the cell lysate. The hybridization complex is shown schematically in FIG. 10.

Hybrid complexes were captured out of solution using magnetic particles by a reversible target capture (RTC) procedure. Briefly, submicron-sized magnetic particles that have short lengths of poly deoxythymidine (poly dT) on their surfaces were added to the hybridization solution and incubated to allow the poly dA moiety of the capture probe to anneal to the oligo dT on the magnetic particles. This, in turn, "captures" the hybrid complexes onto the surface of the magnetic particles as shown schematically in FIG. 10.

The magnetic particles were washed to remove MDV probes that were non-specifically absorbed to their surfaces. The wash buffer (1.5M GuSCN, 100 mM Tris, 10 mM EDTA, 0.5% sarkosyl, 0.5% BSA, 0.01% antifoam, pH 7.9) was added to the particle suspension. The particles were mixed well by vortexing and then drawn to the walls of the tube using a magnetic separation device (GENE-TRAK Systems). The used wash buffer was removed by aspiration and discarded. The particles were resuspended in fresh wash buffer and washed by the above procedure (vortexing, magnetic separation, aspiration) twice more. Finally, the hybrid complexes were released from the magnetic particles by resuspending the particles in a release buffer (3.25M GuSCN, 100 mM Tris, 65 mM EDTA, 0.5% BSA, 0.5% sarkosyl, pH 7.8) which disrupts the poly dA-oligo dT interaction of the capture probes and magnetic particles. The magnetic particles again were drawn to the sides of the tube using the magnetic separator. This time the buffer phase, which contained the released hybrid complexes, was transferred to a clean tube which contained a fresh aliquot of dT-coated magnetic particles. The first set of particles which, even after the extensive washing described above, still had residual MDV probe non-specifically absorbed to their surfaces were discarded.

The GuSCN concentration of the eluted hybrid complex solution was reduced from 3.25M contained in the release buffer to 1.5M by dilution. This allows the poly dA-oligo dT bonds between the capture probe and particle to reform, thereby recapturing the hybrid complex on the fresh set of particles. The triple wash cycle described above then was repeated for this set of particles, following which the hybrid complexes were released from the particles and recaptured onto a third set of fresh particles. The triple wash cycle was repeated for this set of particles. Following, this regime of "passing" the hybrid complexes from used to clean particles and extensive washing, only extremely low levels of MDV RNA probe which was not specifically bound to the target nucleic acid remains in the assay. Each round of cycling (i.e., each passage to a fresh set of particles) reduces the amount of non-specifically bound MDV probe about 1000-fold.

Finally, in preparation for Qβ amplification, the hybrid complexes (still on the final set of particles) are washed three times with a buffer containing 50 mM Tris, 1 mM EDTA, 300 mM KCl, and 0.1% NP40, to remove any traces of GuSCN which inhibits Qβ replicase, and then released from the particles by incubating in the above buffer lacking any KCl. An aliquot of the eluate containing the hybrid complexes (with MDV probes still bound to the target nucleic acid) was used to initiate a Qβ replicase amplification reaction according to the procedure given in Example 1 (i.e., 3 ug/ml propidium iodide, 90 mM Tris, 14 mM MgCl$_2$, 0.4 mM each ATP, GTP, UTP, and CTP, and 1.2 μg of Qβ replicase).

Figure 11:
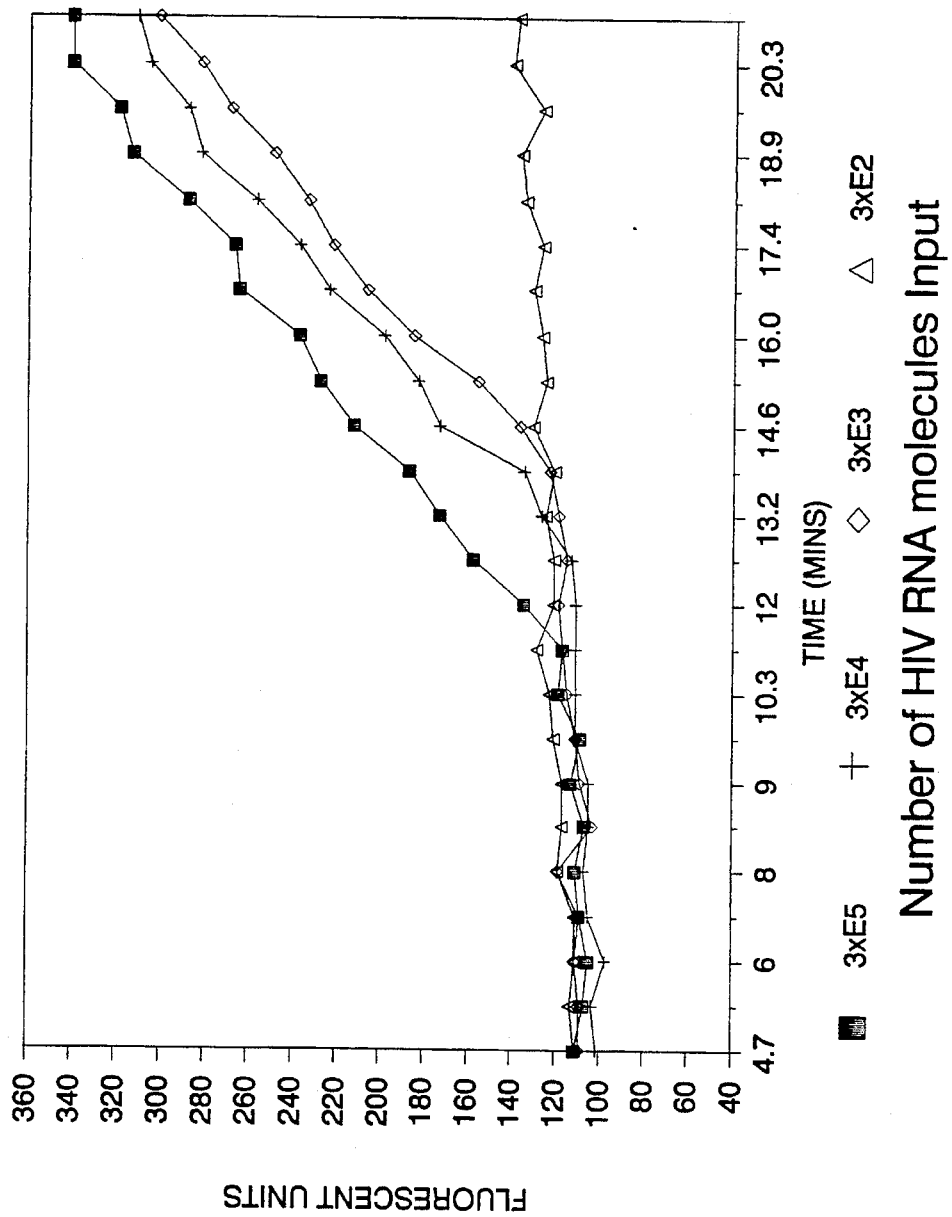
FIG. 11 is a graph illustrating the results of a Qβ replicase amplified reversible target capture assay for HIV.

The reaction was incubated at 37° C. in a fluorometer, which continuously measured the increase in fluorescence as the reaction progressed. As more MDV RNA was made during the course of the Qβ replicase reaction, an easily measurable increase in fluorescence occurred due to the association of the dye with the newly synthesized MDV molecules. This increase was detected and measured by the fluorometer over the time course of the reaction (FIG. 11).

The amount of fluorescence is proportional to the amount of MDV RNA present. The length of time it takes to detect a measurable increase in fluorescence above the background level varies inversely with the amount of MDV RNA present at the beginning of the Qβ replicase reaction. This, in turn, is proportional to the amount of target nucleic acid which originally was present in the sample since MDV probe only persists through the RTC procedure by virtue of being associated with target nucleic acid. The major function of the RTC procedure is to remove MDV RNA probe which is not specifically hybridized to target nucleic acid. Therefore, not only is the presence or absence of a target nucleic acid in a sample detectable using this process, but some measure of its abundance also can be obtained.

Example 6

A Qβ Amplified Reversible Target Capture Assay for the Detection of *Chlamydia trachomatis*

An MDV construct containing a sequence specific for *Chlamydia trachomatis* 16S rRNA was constructed and used as a detector probe in a reversible target capture assay according to the method described in Example 5. For construction of the Chalmydia specific propidium iodide resistant MDV RNA detection probe, a Chlamydia specific oligonucleotide sequence, rather than a HIV-specific oligonucleotide as in Example 5, was appended to the 3' end of a propidium iodide resistant MDV RNA using essentially the same cloning and in vitro transcription protocol. The RNA probe is similar to the HIV probe shown in FIG. 9, except for the exchange of the 3' B probe specific portion. A *Chlamydia trachomatis* 16S rRNA specific oligonucleotide was synthesized on an Applied Biosystems 380A Oligonucleotide Synthesizer and dA tailed for use as a capture probe in the assay. The capture and detection probes are designed so that they hybridize to adjacent sites in the *C. trachomatis* (*C. trachomatis*) 16S rRNA.

*C. trachomatis* serovar K (ATCC VR-887) was obtained from the American Type Culture Collection and grown in McCoy cells. Elementary bodies (EB), which are the spore-like infectious form of the bacterium, were purified from the McCoy cells, quantitated by immunofluorescence and stored at −20° C. until use according to the method described by Phillips et al., in *Journal of Infectious Diseases*, 156:575–581 (1987). Other forms of this obligately intracellular parasite, such as the vegetative Reticulate Bodies, are much more difficult to purify intact from the host (McCoy) cells, and so are not nearly as amenable to quantitation as the relatively hardy elementary bodies. However, experiments similar to that reported here have been performed on infected McCoy cells and Chlamydia positive cervical swabs, with similar results.

A dilution series of the EBs ranging from $1\times10^5$ to $1\times10^2$ was prepared and assayed by nucleic acid hybridization using the probes described above. Approximately $1\times10^5$ *Escherichia coli* (*E. coli*) cells were also added to each of the EB samples as a source of mock competitor nucleic acid. Except for the capture and detection probes, the methods and materials used in this Example were essentially the same as those described for the HIV Amplified Assay in Example 5.

The detection and quantification of MDV detector probe molecules from the EB samples also were carried out through in vitro amplification of the MDV RNA probe according to the procedure described in Example 5.

The detection of approximately 1000 EBs (equivalent to approximately 10,000 16S rRNA targets, assuming 100 rRNA molecules per EB) was possible after observing the relationship of response time to the number of elementary bodies of this organism in the assay. The mean response time of 15.3 minutes for the 1000 EB sample represents a typical response time when about 1000 MDV reporter molecules are added directly to control Qβ replicase reactions without intervening target cycling.

Equivalents

Those skilled in the art will recognize, or be able to ascertain, using no more than routine experimentation, equivalents to the specific embodiments of the invention described specifically herein. Such equivalents are intended to be encompassed in the scope of the following Claims.

I claim:

1. A hybridization assay for the detection of a target nucleic acid, comprising the steps of:
    a) providing a replicatable mutant MDV RNA molecule linked to an RNA probe sequence which is substantially complementary to a portion of the target nucleic acid, the mutant MDV RNA molecule being resistant to a fluorescent dye which binds to wild type MDV RNA and which inhibits replication of wild type MDV RNA by Q-beta replicase;
    b) contacting the mutant MDV RNA molecule with a solution to be tested for the presence of the target nucleic acid, under conditions appropriate for hybridization between complementary nucleic acid sequences, thereby forming a mutant MDV RNA-target nucleic acid complex;
    c) isolating the mutant MDV RNA target nucleic acid complex;
    d) contacting the mutant MDV RNA-target nucleic acid complex with Q-beta replicase, in the presence of the fluorescent dye which binds to wild type MDV RNA, under conditions appropriate for amplification of the mutant MDV RNA and inhibition of replication of wild type MDV RNA; and
    e) detecting amplified mutant MDV RNA as an indication of the presence of target nucleic acid in the solution to be tested.

2. A hybridization assay of claim 1, wherein the fluorescent dye which binds to wild type MDV RNA thereby inhibiting replication by Q-beta replicase, is selected from the group consisting of ethidium bromide, ethidium bromide homodimer, propidium iodide, proflavine, quinacrine, dimidium bromide and acridine orange.

3. A hybridization assay of claim 1, wherein amplified mutant MDV RNA is detected by exposing amplified mutant MDV RNA to light of an appropriate wavelength to stimulate fluorescence of the fluorescent dye which binds to wild type MDV RNA and detecting the fluorescence.

4. A method of claim 3 wherein the probe sequence is attached to the 5' or 3' end of the replicatable mutant MDV RNA.

5. A method of claim 3 wherein the probe sequence is present as a midsequence insertion in the replicatable mutant MDV RNA at a site which does not inhibit replication.

6. A hybridization assay of claim 1 wherein the amplification in step d) is carried out with reagents appropriate for the labeling of the amplified product with a reporter group or a member of a specific binding pair, and the reporter group or member of the specific binding pair is detected as an indication of mutant MDV RNA amplification.

* * * * *